United States Patent
Robinson et al.

(10) Patent No.: US 9,427,506 B2
(45) Date of Patent: Aug. 30, 2016

(54) SYSTEM AND METHOD FOR LOCATING FLUID LEAKS AT A DRAPE USING SENSING TECHNIQUES

(75) Inventors: Timothy Mark Robinson, Basingstoke (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 1082 days.

(21) Appl. No.: 13/075,676

(22) Filed: Mar. 30, 2011

(65) Prior Publication Data

US 2011/0245682 A1     Oct. 6, 2011

Related U.S. Application Data

(60) Provisional application No. 61/319,344, filed on Mar. 31, 2010.

(51) Int. Cl.
| | |
|---|---|
| *H04N 7/18* | (2006.01) |
| *A61M 1/00* | (2006.01) |
| *A61B 19/00* | (2006.01) |
| *A61B 5/00* | (2006.01) |

(Continued)

(52) U.S. Cl.
CPC .............. *A61M 1/0088* (2013.01); *A61B 1/041* (2013.01); *A61B 1/05* (2013.01); *A61B 5/0059* (2013.01); *A61B 19/5244* (2013.01); *A61M 1/0025* (2014.02); *G01M 3/002* (2013.01); *G01M 3/20* (2013.01); *H04N 7/18* (2013.01); *A61M 2205/15* (2013.01)

(58) Field of Classification Search
CPC ........ A61B 1/041; A61B 1/05; A61B 5/0059; A61B 19/5244; H04N 7/18; H04N 2005/2255
USPC ......................................... 348/77, 68, 69, 65
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

International Search Report and Written Opinion date mailed May 30, 2011; International PCT Application No. PCT/US2011/030698.

(Continued)

*Primary Examiner* — Shawn An (57) ABSTRACT

A system and method for determining location of a fluid leak at a drape of a reduced pressure delivery system being used on a tissue site of a patient may include applying a reduced pressure to the tissue site of the patient. The drape may be imaged to generate image data, and a determination of a location of a fluid leak of the drape may be made from the image data. As a result of the determination of the location of the fluid leak, the drape may be corrected. The imaging may be made in a non-visible spectrum. The non-visible spectrum may be in an IR spectrum or UV spectrum. In one embodiment, a fluid, such as compressed air, may be applied to the dressing via the interface between the drape and tissue of the patient to improve imaging in the non-visible spectrum.

13 Claims, 8 Drawing Sheets

(51) Int. Cl.
*A61B 1/05* (2006.01)
*A61B 1/04* (2006.01)
*G01M 3/00* (2006.01)
*G01M 3/20* (2006.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 8,135,475 B2* | 3/2012 | Kreindel et al. ............... 607/99 |
| 8,500,718 B2* | 8/2013 | Locke ............... A61M 5/1415 604/543 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0065314 A1* | 4/2003 | Altshuler ............... A61B 18/203 606/9 |
| 2004/0073151 A1 | 4/2004 | Weston |
| 2005/0045189 A1* | 3/2005 | Jay ............... A61B 5/0059 128/898 |
| 2005/0272973 A1* | 12/2005 | Kawano ............... A61B 1/00036 600/102 |
| 2007/0265586 A1 | 11/2007 | Joshi et al. |
| 2009/0080757 A1 | 3/2009 | Roger et al. |
| 2009/0227969 A1 | 9/2009 | Jaeb et al. |
| 2011/0130642 A1* | 6/2011 | Jaeb ............... A61M 5/1415 600/407 |
| 2014/0028824 A1* | 1/2014 | Kubo ............... A61B 5/0071 348/77 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| JP | 04-279850 | 10/1992 |
| JP | 2002-210742 | 7/2002 |
| JP | 2003-130752 | 5/2003 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |

(56) References Cited

FOREIGN PATENT DOCUMENTS

| WO | WO 93/24820 A1 | 12/1993 |
|---|---|---|
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 2008/036345 A1 | 3/2008 |
| WO | WO 2008/041926 A1 | 4/2008 |
| WO | WO 2008/143628 A1 | 11/2008 |

OTHER PUBLICATIONS

N.A. Bagautdinov, "Variant of External Vacuum Aspiration in the Treatment of Purulent Diseases of the Soft Tissues," *Current Problems in Modem Clinical Surgery: Interdepartmental Collection*, edited by V. Ye Volkov et al. (Chuvashia State University, Cheboksary, U.S.S.R. 1986);pp. 94-96 (certified translation).

Louis C. Argenta, MD and Michael J. Morykwas, PhD; "Vacuum-Assisted Closure: A New Method for Wound Control and Treatment: Clinical Experience"; Annals of Plastic Surge , vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, Ma 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Đukić, Ž. Maksimović, Đ. . Radak, and P. Peška, "Vacuum Therapy in the Treatment of Peripheral Blood Vessels," *Timok Medical Journal* 11 (1986), pp. 161-164 (certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

\* cited by examiner

SYSTEM AND METHOD FOR LOCATING FLUID LEAKS AT A DRAPE USING SENSING TECHNIQUES

CROSS-REFERENCE TO RELATED APPLICATIONS

This application claims the benefit of U.S. Provisional Application No. 61/319,344, filed Mar. 31, 2010, which is incorporated herein by reference in its entirety.

BACKGROUND OF THE INVENTION

1. Field of the Invention

This invention relates generally to a system and method of promoting tissue growth, and more specifically, a method for detecting and correcting fluid leaks at a drape positioned at a tissue site being treated by a reduced pressure delivery system.

2. Description of Related Art

Tissue growth and wound healing of patients has been shown to be accelerated through the use of applying reduced pressure to a tissue site. Reduced pressure delivery systems operate to form such a reduced pressure at a tissue site of a patient. This form of wound healing can be readily integrated into a clinician's wound healing procedures. Reduced pressure tissue therapy optimizes patient care and decreases costs associated with treatment of patients having traumatic and chronic wounds. Reduced pressure therapy can be administered in hospitals, community settings, such as assisted living complexes and convalescences homes, or homes of patients.

Reduced pressure delivery to a wound or tissue site promotes wound healing and/or tissue growth, in part, by removing infectious materials and other fluids from the wound or tissue site. Reduced pressure treatment further promotes tissue growth by imposing forces on the tissue, thereby causing micro-deformation of the tissue, which is believed to contribute to the development of granulation tissue at the tissue site. The forces imposed on the tissue site by the delivery of reduced pressure further encourages improved blood flow at the tissue site, which further assists in the growth of new tissue.

Reduced pressure delivery systems generally use a vacuum pump to apply a reduced pressure via a reduced pressure conduit to a tissue site. A manifold is often used at the tissue site to help evenly distribute the reduced pressure. A drape is typically used to cover the manifold and form a seal with surrounding tissue of the tissue site to which the reduced pressure is being applied. So that the reduced pressure remains constant and accurate, thereby providing optimum tissue growth and/or therapy, the drape is to be interfaced and maintained with the surrounding tissue of the tissue site to prevent fluid leaks, such as air leaks. In the event that a fluid leak results during installation of the drape or during treatment, clinicians often find it difficult to isolate the precise location of the fluid leak. If the fluid leak is not corrected, then the performance of the reduced pressure delivery system is reduced and full treatment potential is not realized.

SUMMARY OF THE INVENTION

To overcome the problem of locating fluid leaks of a drape being used on a tissue site of a patient, the principles of the present invention provide for detecting location of and correcting fluid leaks at the drape of reduced pressure delivery systems. More specifically, the principles of the present invention provide for using one or more image sensing techniques (e.g., IR sensing, UV sensing, and temperature sensing) for locating fluid leak locations of the drape. By being able to locate fluid leaks at the drape (e.g., at an interface between the drape and tissue of the patient), optimum therapeutic results may be produced.

One embodiment of a process for determining location of a fluid leak at a drape of a reduced pressure delivery system being used on a tissue site of a patient may include applying a reduced pressure to the tissue site of the patient. The drape may be imaged to generate image data, and a determination of a location of a fluid leak of the drape may be made from the image data. As a result of the determination of the location of the fluid leak, the drape may be corrected. The imaging may be made in a non-visible spectrum. The non-visible spectrum may be in an IR spectrum or UV spectrum. In one embodiment, a fluid, such as compressed air, may be applied to the dressing via the interface between the drape and tissue of the patient to improve imaging in the non-visible spectrum.

One embodiment of a system for determining location of a fluid leak at a drape of a reduced pressure delivery system and tissue of a patient may include a processing unit that is configured to control operation of the reduced pressure delivery system. An input/output (I/O) unit may be in communication with the processing unit. An imaging system may be configured to image the drape at the tissue site of a patient and to communicate image data to the processing unit via the I/O unit. The imaging system may further be configured to generate image data having different shades or colors based on temperature or otherwise to enable a user to view the image data to determine a location of the fluid leak. The reduced pressure delivery system may further be configured to display the image data on an electronic display. The imaging system may include an IR and/or UV sensor for capturing IR and/or UV spectral image data.

Another embodiment of a process for determining location of a fluid leak at a drape of a reduced pressure delivery system being used on a tissue site of a patient may include applying a dressing to a tissue site of the patient. The drape may be applied over the dressing and tissue site of the patient, where at least one of the dressing and drape may be coated with a coating that changes color in response to an environmental factor. The environmental factor may include pressure and temperature. A fluid leak of the drape may be located in relation to a region of the coating changing color and corrected. Fluid may be applied to the interface, where the fluid may include at least one of compressed air, $CO_2$, fluorocarbon, and butane. In one embodiment, the fluid may be in an aerosol form.

BRIEF DESCRIPTION OF THE DRAWINGS

A more complete understanding of the method and apparatus of the present invention may be obtained by reference to the following Detailed Description when taken in conjunction with the accompanying Drawings wherein.

DETAILED DESCRIPTION OF THE PRESENT INVENTION

Figure 1:
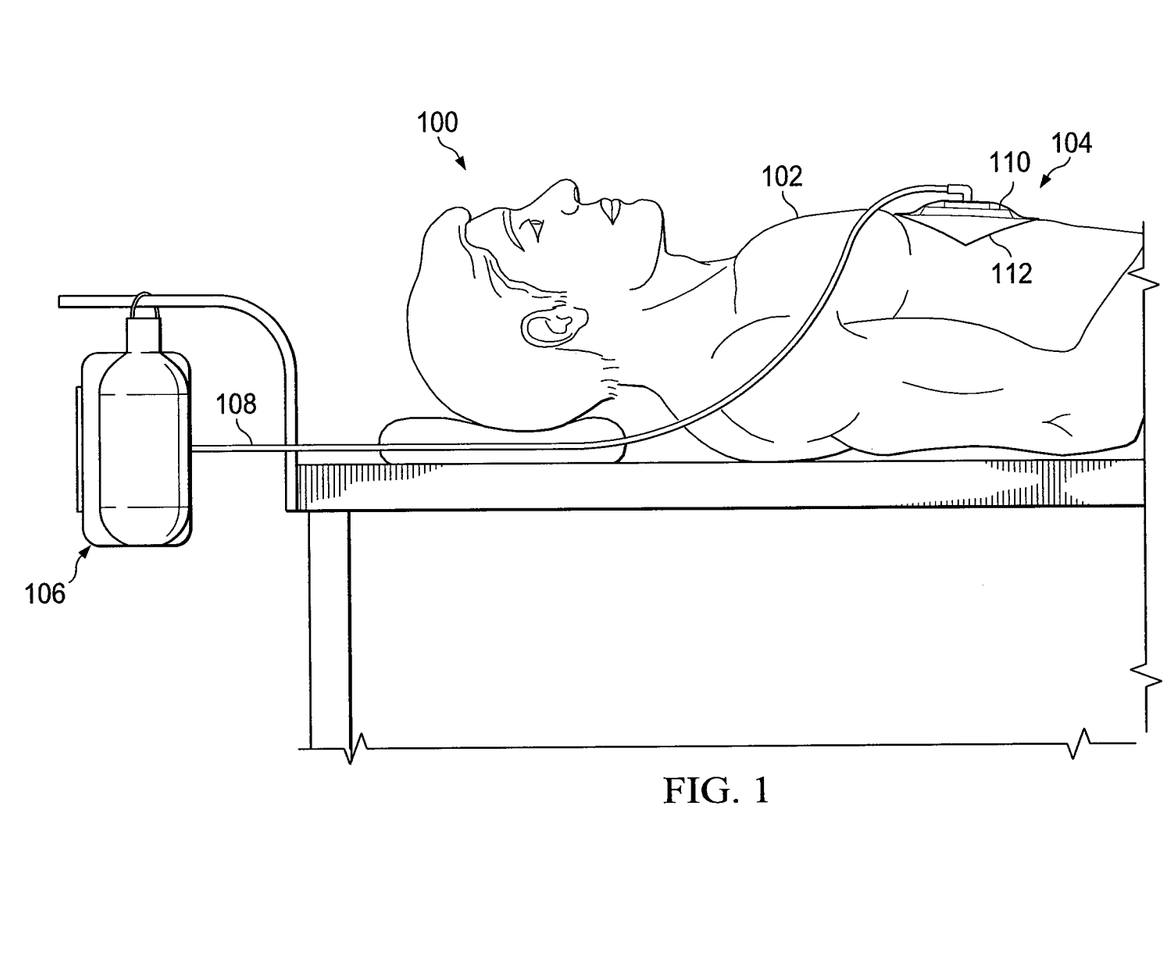
FIG. 1 is an illustration of an illustrative configuration of a patient being treated using a reduced pressure delivery system.

With regard to FIG. 1, a setup 100 for treating a patient 102 is shown. The patient is receiving reduced pressure treatment at a tissue site 104 by a reduced pressure delivery system 106. The reduced pressure delivery system 106 includes a reduced pressure conduit 108 that extends from the reduced pressure delivery system 106 to the tissue site 104. At the tissue site 104, a reduced pressure dressing or distribution manifold 110 may be fluidly connected to the reduced pressure conduit 108. In addition, a drape 112 may be placed over the tissue site 104 and distribution manifold 110. The drape 112 may be a flexible material that is impermeable to gases to prevent air or other fluids from entering or exiting the tissue site 104 during reduced pressure treatment. In one embodiment, the drape is a transparent film having an adhesive around the perimeter, as understood in the art. Alternative embodiments of the drape may be utilized in accordance with the principles of the present invention to enable a clinician to sense fluid leaks between the drape 112 and tissue of the patient 102.

As used herein, the term "flexible" refers to an object or material that is able to be bent or flexed. Elastomer materials are typically flexible, but reference to flexible materials herein does not necessarily limit material selection to only elastomers. The use of the term "flexible" in connection with a material or reduced pressure delivery apparatus in accordance with the principles of the present invention generally refers to the material's ability to conform to or closely match the shape of a tissue site. For example, the flexible nature of a reduced pressure delivery apparatus used to treat a bone defect may allow the apparatus to be wrapped or folded around the portion of the bone having the defect.

The term "fluid" as used herein generally refers to a gas or liquid. One example of a gas is air. One example of liquid is water.

The term "manifold" as used herein generally refers to a substance or structure that is provided to assist in applying reduced pressure to, delivering fluids to, or removing fluids from a tissue site. A manifold typically includes a plurality of flow channels or pathways that interconnect to improve distribution of fluids provided to and removed from the area of tissue around the manifold. Examples of manifolds may include, without limitation, devices that have structural elements arranged to form flow channels, cellular foams, such as open-cell foam, reticulated foam, porous tissue collections, and liquids, gels and foams that include or cure to include flow channels.

As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Reduced pressure may initially generate fluid flow in the manifold, reduced-pressure conduit, and proximate the tissue site. As the hydrostatic pressure around the tissue site approaches the desired reduced pressure, the flow may subside, and the reduced pressure may be maintained. Unless otherwise indicated, values of pressure stated herein are gauge pressures. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, unless otherwise indicated, an increase in reduced pressure or vacuum pressure typically refers to a relative reduction in absolute pressure.

The term "tissue site" as used herein refers to a wound or defect located on or within any tissue, including but not limited to, bone tissue, adipose tissue, muscle tissue, neuro tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

The term "clinician" is used herein as meaning any medical professional, user, family member of a patient, or patient who interacts or interfaces with a reduced pressure delivery system.

Figure 2:
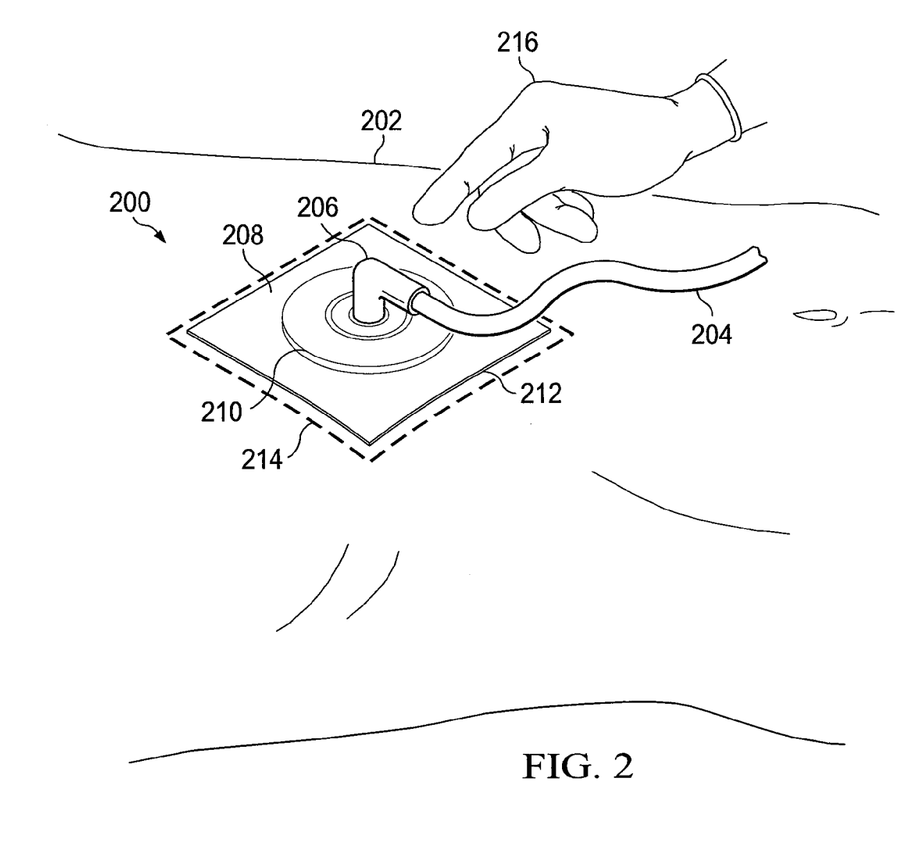
FIG. 2 is an illustration of an illustrative drape covering a tissue site to which reduced pressure is being applied by a reduced pressure delivery system.

With regard to FIG. 2, a tissue site 200 on a person's body 202 is receiving reduced pressure therapy from a reduced pressure delivery system (not shown). The reduced pressure delivery system is connected to a reduced pressure conduit 204 and in fluid communication with a distribution manifold (not shown), either directly or via an adapter 206. A drape 208 may be configured to cover the distribution manifold, which is shown to be pressing into the drape 208 to form an outline 210. The drape 208 covers the tissue site 200, thereby helping to maintain a seal at the tissue site so that fluids, such as air, cannot enter or exit the tissue site. By preventing fluids from entering or exiting the tissue site 200, the tissue site 200 may receive maximum benefit of the reduced pressure therapy, including minimizing chance for additional infection and improving growth of tissue.

In establishing a dressing, which may include the distribution manifold and drape 208, at the tissue site 200, a clinician may apply the dressing and apply a force to the drape 208 during operation of the reduced pressure delivery system. By applying a force along outer edges of the drape 208, the clinician may create or otherwise alter a seal at an intersection 212 of the drape 208 and tissue 214 surrounding the tissue site 200. In the event that the seal is not completely formed or a fluid leak develops at the drape 208, the clinician may press his or her finger 216 along the outer edges 212 of the drape 208 to improve or re-establish the seal. Because locating a fluid leak at the drape 208 is often difficult in practice, the principles of the present invention provide a system and method for determining location of the fluid leak, as further described herein with respect to FIGS. 4-8.

Figure 3:
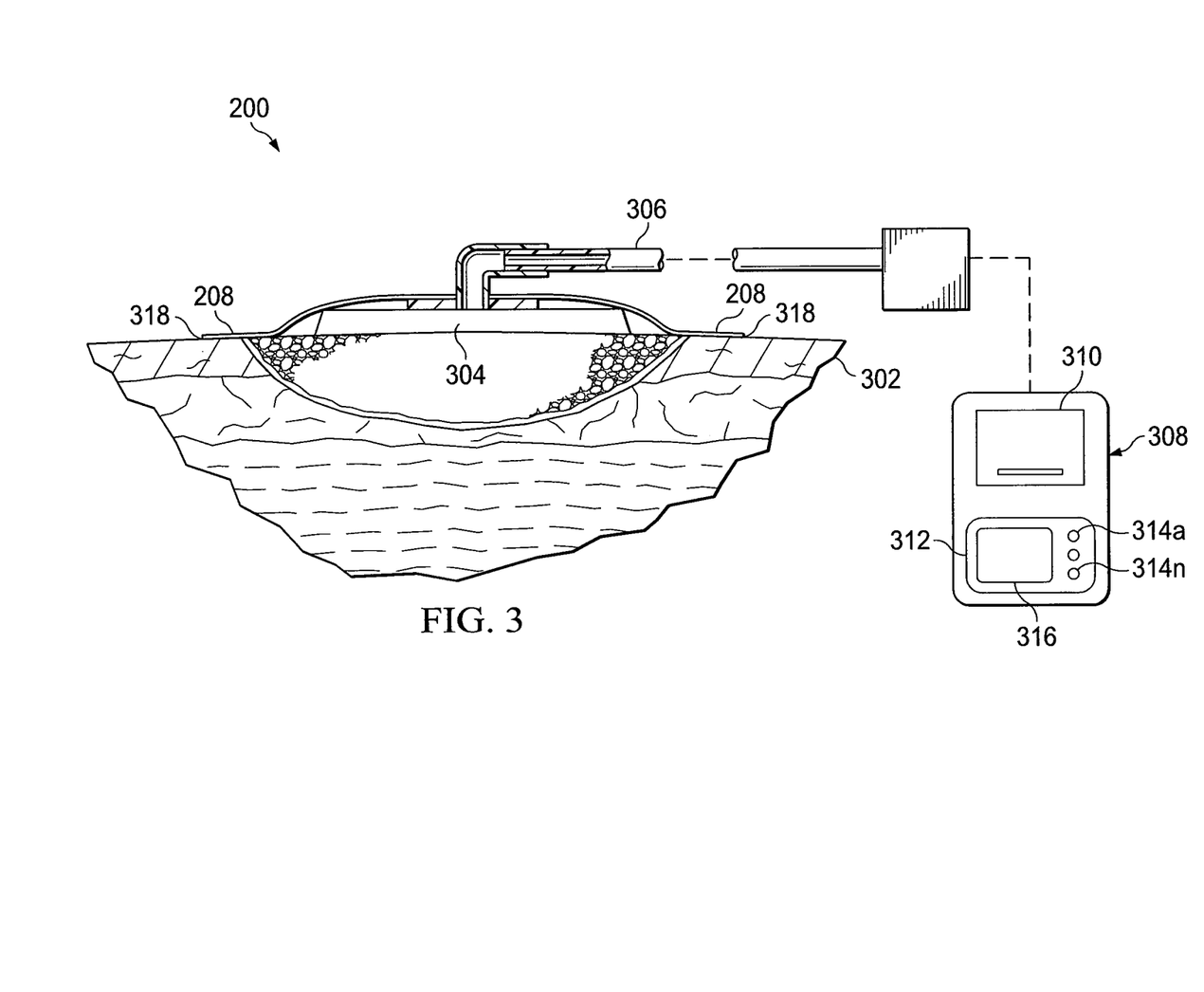
FIG. 3 is an illustration of an illustrative drape covering a tissue site to which reduced pressure is being applied by a reduced pressure delivery system.

With regard to FIG. 3, a cutout view of the tissue site 200 is provided to show the drape 208 extending over healthy tissue 302 surrounding the tissue site 200. The drape 208 extends over manifold 304, which is in fluid communication with reduced pressure conduit 306. The reduced pressure conduit 306 is further in fluid communication with reduced pressure delivery system 308. The reduced pressure therapy system 308 may include a vacuum pump 310 and electronic display 312. The electronic display 312 may include control elements 314a-314n (collectively 314) that may be used by a user operating the reduced pressure delivery system 308. In addition or alternatively, the electronic display 312 may include a touch-screen electronic display 316 that enables the user to interface with and operate the reduced pressure delivery system 308.

The drape 208 that extends over the healthy tissue 302 forms a seal at an intersection or interface 318 where the healthy tissue 302 and drape 208 contact one another. If a fluid leak develops at the intersection 318 (i.e., at the tissue site 200), then a fluid leak sensor (not shown) may generate and communicate a fluid leak signal. The fluid leak signal may be indicative of a fluid parameter indicative of or responsive to the fluid leak crossing a predetermined threshold level. A processing unit (not shown) may respond by generating a fluid leak alarm in an audible and/or visual manner. For example, a buzzer, bell, recorded message, or other audible sound may be generated to alert a clinician that a fluid leak has occurred at the drape 208. To locate the fluid leak at the drape 208, a fluid leak location mode may be automatically or manually entered at the reduced pressure delivery system 308. The fluid leak location mode may be used to assist a clinician in identifying a fluid leak location by generating a response, such as an audible response, to the clinician's apply a force, such as pressing a finger along the drape 208 (e.g., at the intersection 318), in an attempt to seal the fluid leak. Although it is generally understood that fluid leaks primarily occur at the intersection of the drape and tissue of a patient, it should be understood that the principles of the present invention may similarly be utilized to detect openings, such as punctures, that exist on the drape itself.

Figure 4:
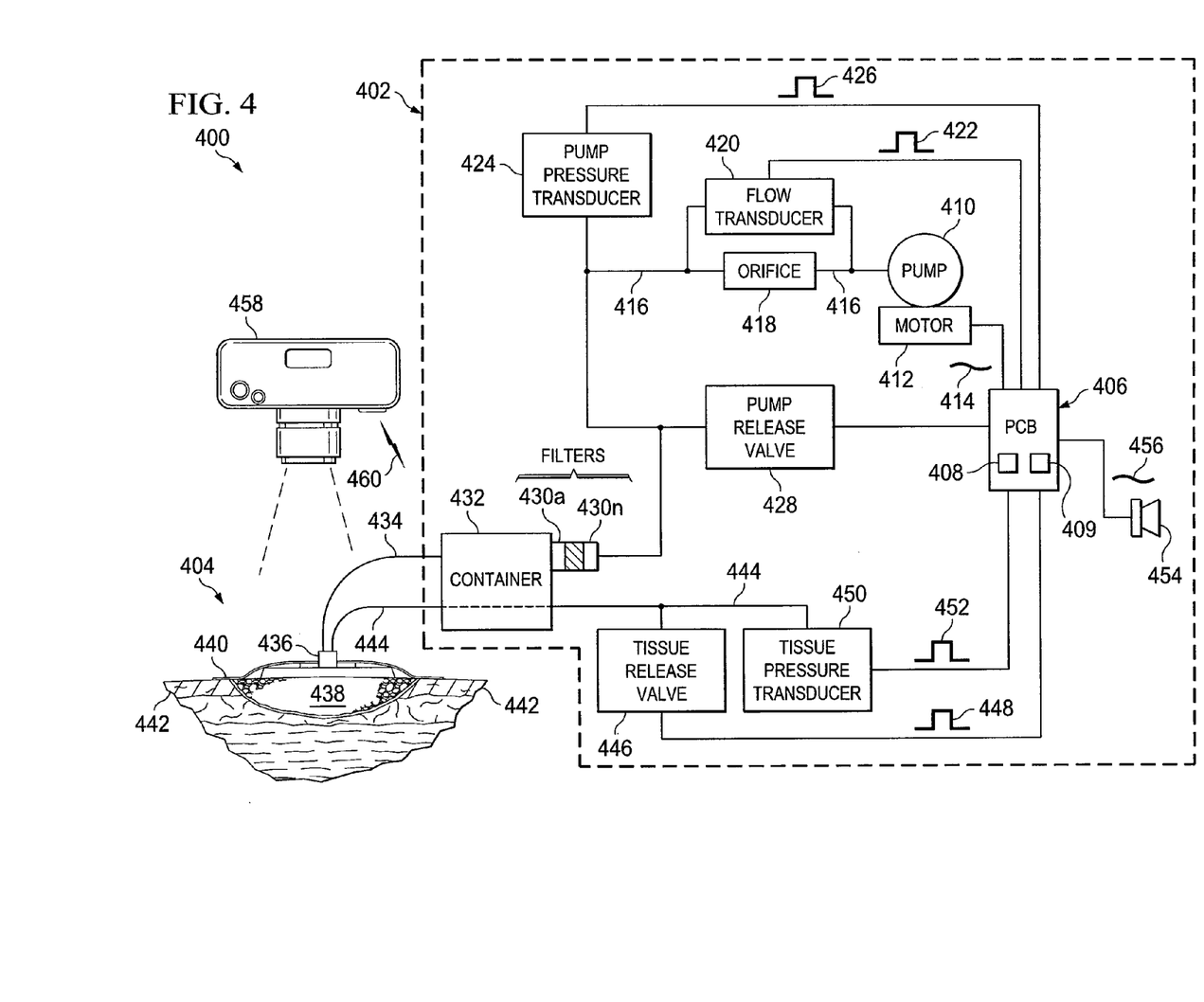
FIG. 4 is a block diagram of an illustrative reduced pressure delivery system configured to apply reduced pressure to a tissue site and notify a clinician that a fluid leak is occurring at the drape.

With regard to FIG. 4, a configuration 400 of a reduced pressure delivery system 402 is shown to be operating to apply a reduced pressure to tissue site 404. The reduced pressure delivery system 402 includes a printed circuit board (PCB) 406 that includes a processing unit 408. The processing unit 408 may include one or more processors, logic, analog components, or any other electronics that enable signals including information, such as fluid pressure at a tissue site, to be received. The processing unit 408 may process the information provided by the signals. For example, a fluid leak signal may be received by the processing unit 408 and a fluid leak alarm and/or fluid leak location process may be driven by the processing unit 408. An input/output (I/O) unit 409 may be included with or separate from the PCB 406, where the I/O unit 409 may provide for wired and/or wireless communications with one or more peripheral devices, such as a digital camera, remote control device, or other data collection or control device. The I/O unit 409 may utilize RF, infrared, WiFi®, Bluetooth®, or any other wireless or wireline communications protocol, as understood in the art.

The reduced pressure delivery system 402 may further include a pump 410, such as a vacuum pump, that may be driven by a motor 412. The motor 412 may be in electrical communication with the PCB 406 and respond to control signals 414 generated by the PCB 406. The pump 410 may be fluidly connected to a reduced pressure conduit 416. The reduced pressure conduit 416 may include an orifice 418 that limits flow and creates a pressure drop for measurement thereof. In parallel with the orifice 418 is a flow transducer 420 that may be configured to determine flow rate of fluid passing through the reduced pressure conduit 416 by using the orifice 418. The flow transducer 420 is fluidly connected to the reduced pressure conduit 416 and configured to generate a flow rate signal 422 including information indicative of flow rate of a fluid within the reduced pressure conduit 416. The flow rate signal 422 may be digital or analog.

A pump pressure transducer 424 may be connected to reduced pressure conduit 416 to convert pressure in the reduced pressure conduit 416 and communicate a pump pressure signal 426 including information indicative of fluid pressure in the reduced pressure conduit 416 to the PCB 406. The pump pressure signal 426 may be digital or analog. A pump release valve 428 may also be connected to the reduced pressure conduit 416 and be configured to release pressure from the reduced pressure conduit 416 in case of an emergency situation or otherwise.

The reduced pressure delivery system 402 may further include one or more filters 430a-430n (collectively 430) that are in fluid communication with the reduced pressure conduit 416. The filters 430 may be in fluid communication with container 432, which is used to collect fluids from tissue site 404. The filters 430 may be configured to prevent fluids collected in the container 432 from entering the reduced pressure conduit 416. The container 432 may further be in fluid communication with reduced pressure conduit 434. Although shown as separate conduits, the reduced pressure conduits 416 and 434 may be the same or different material and have the same or different dimensions. The reduced pressure conduit 434 may connect to or be in fluid communication with an adapter 436, which may be connected to a distribution manifold 438 to evenly distribute reduced pressure across the tissue site 404. Drape 440, which extends over the tissue site and onto tissue 442 surrounding the tissue site 404 being treated by the reduced pressure, is used to form a seal to form and maintain reduced pressure at the tissue site 404.

A feedback reduced pressure conduit 444 may pass through container 432. A tissue release valve 446 may be connected to the feedback reduced pressure conduit 444 to enable pressure to be released at the tissue site 404 in response to a command signal 448 generated by the processing unit 408. The command signal 448 may be generated by the processing unit 408 in response to the processing unit 408 receiving a sensor signal, such as flow rate signal 422, crossing a threshold level. Alternatively, the command signal 448 may be generated in response to a clinician selectively stopping the reduced pressure delivery system 402 via a user interface (not shown). Other events, such as a treatment cycle completing, may cause the processing unit to generate the command signal 448 to activate the tissue release valve 446. In another example, a tissue pressure transducer 450 may be used to convert pressure sensed at the tissue site 404 and provide a feedback signal 452 to the processing unit 408 on the PCB 406. In response to the processing unit 408 determining that pressure at the tissue site 404 sensed by the tissue pressure transducer 450 is above a threshold value, the processing unit 408 may communicate command signal 448 to the tissue release valve 446 for release of tissue pressure.

An electronic speaker 454 may be in electrical communication with the PCB 406 to generate an audible sound. In the event that the processing unit 408 determines that a fluid parameter, such as pressure at the tissue site 404 or flow rate of fluid through the reduced pressure conduit 416, crosses a threshold value, a signal 456 may be generated by the PCB 406 and communicated to the electronic speaker 454 to create an audible sound. For example, the processing unit 408 may determine that a fluid leak exists at the tissue site 404 by a fluid rate increasing above a flow rate threshold level. In response to determining that the flow rate level sensed by a flow transducer, such as flow transducer 420, the processing unit 408 may generate the signal 456, such as an alert signal, and communicate the alert signal to the electronic speaker 454 to notify a clinician that a problem exists. In another example, a sensor, such as tissue pressure transducer 450, may sense a fluid parameter at the tissue site 404 and the processing unit 408 may determine that the pressure at the tissue site 404 decreases. Still yet, rather than directly sensing a fluid parameter, an indirect measurement may be performed by measuring duty cycle or power of the pump 410 to determine approximate fluid flow.

The processing unit 408 may be selectively programmed or commanded into a fluid leak location mode that notifies the clinician or patient to locate the fluid leak location utilizing at least one of the principles of the present invention. In notifying the clinician or patient, a notification on the electronic display may provide instructions (e.g., "use IR imaging camera to take photo of drape/dressing"), an audible notification may be generated (e.g., sequence of tones, recorded speech with instructions, or synthesized audible instructions). Still yet, the clinician may be instructed to visually inspect the dressing to identify color changes if the dressing is coated with pressure or temperature sensitive paint, dye, or other coating. Other elements, such as a strip of metal with pressure or temperature sensitive paint coating the strip, may be included within the dressing (e.g., sandwiched between the dressing and drape 440).

In one embodiment, the reduced pressure delivery system 402 may be configured to communicate with a digital camera 458 that may be utilized to take a photograph of the drape 440, distribution manifold 438, and other dressing components (e.g., foam). The digital camera 458 may be configured to take both still and video images. The camera 458 may further be configured to take infrared (IR), ultraviolet (UV), and/or gas presence images that provide the clinician with the ability to visually detect temperature or other non-visible spectrum variations as a result of a fluid leak of the drape 440. The temperature variations provide the clinician with the ability to readily identify leak locations and relative sizes of the leaks by color variations being displayed as a result of gasses entering the drape 440 and dressing expanding and cooling the dressing and drape 440.

The camera 458 may further be configured to timestamp the captured images and communicate the images via a wired (not shown) or wireless communications signal 460 to the reduced pressure delivery system 402 for storage thereat. Alternatively, the captured images may be timestamped and stored by the reduced pressure delivery system 402 in association with a patient's records, which may also include treatment records. The captured images may be stored in association with a patient's records that may also include other treatment parameters, measurements, tissue site images over time, etc. The communication of the captured images from the camera 458 to the reduced pressure delivery system 402 may be performed automatically, semi-automatically, or manually in response to the clinician actively controlling the reduced pressure delivery system 402 and/or camera 458.

Figure 5:
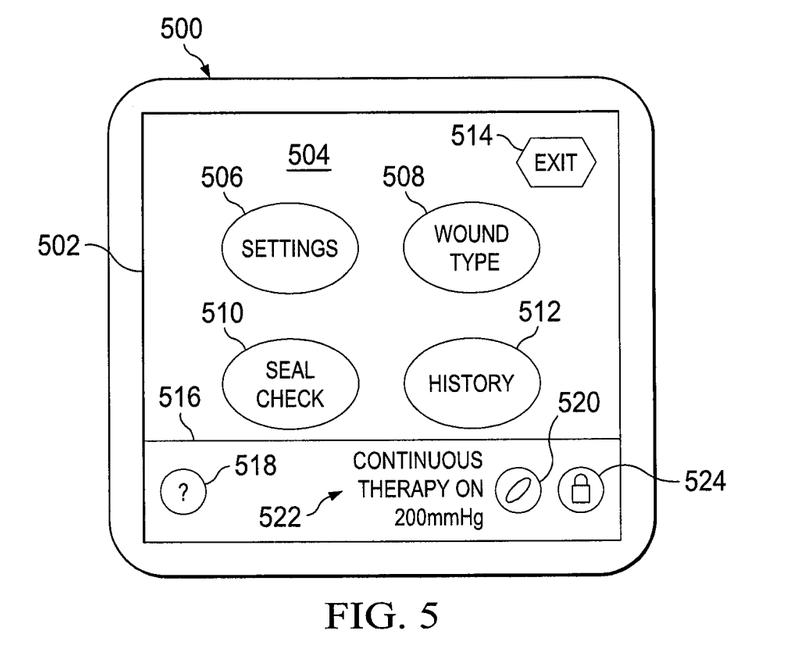
FIG. 5 is a screen shot of an illustrative graphical user interface that enables a clinician to select a "seal check" function to locate fluid leaks that exist at the drape.

With respect to FIG. 5, a reduced pressure delivery system 500 may include an electronic display 502 that is configured to display a graphical user interface (GUI) 504. The GUI 504 may include a number of selectable graphical elements, including a "settings" soft-button 506, "wound type" soft-button 508, "seal check" soft-button 510, and "history" soft-button 512. A user may select any of these functions (i.e., settings, wound type, seal check, or history), to cause the reduced pressure delivery system 500 to present the user with another graphical user interface for performing the selected function. In addition, an "exit" soft-button 514 may be available to the user to exit the current GUI 504. It should be understood that the GUI 504 is illustrative and that other and/or alternative functions and selection elements may be provided to the user.

An information region 516 on the GUI 504 may include selectable graphical elements and display other information in which the user may be interested. For example, a "help" soft-button 518 may be displayed to enable the user to receive help about the reduced pressure delivery system 500 or particular functions currently being displayed on the GUI 504. An "on-off" soft-button 520 may enable a user to selectively turn the reduced pressure delivery system 500 on and off, and information 522 may notify the user of current status of the reduced therapy delivery system 500. For example, the status information 522 may indicate that the reduced therapy delivery system 500 is (i) operating in a continuous therapy mode, (ii) is on, and (iii) is operating to provide a reduced pressure of −200 mmHg. A "lock" soft-button 524 may enable the user to lock the GUI 504 to prevent an inadvertent contact with the GUI 504 to cause the reduced therapy delivery system 500 to respond.

Figure 6A:
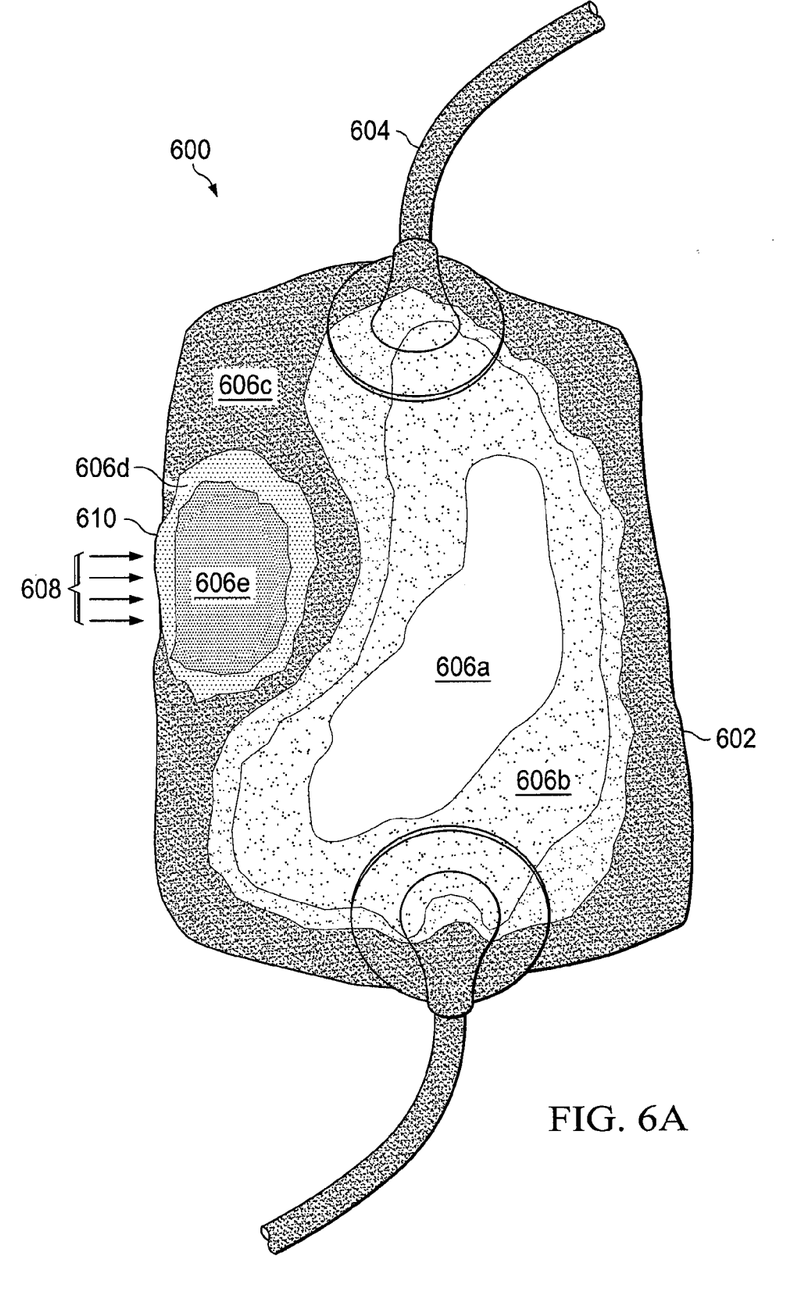
FIG. 6A is an illustration of an illustrative dressing and drape being used to treat a tissue site and in which the drape includes a fluid leak.

With regard to FIG. 6A, an illustration of an IR image 600 of an illustrative tissue site that is covered by a dressing and drape is shown. The IR image 600 shows a drape 602 that covers the tissue site to be in fluid communication with a conduit 604. The IR image 600 shows multiple color/shaded regions 606a-606e that define relative temperatures between the drape and tissue site. Temperature region 606a is the hottest region due to being on surfaces (e.g., foam dressing) in the center of the tissue area. Temperature region 606b is shown to be slightly cooler than temperature region 606a. Temperature region 606c, which is at the interface of the drape 602 and tissue of the patient, is cooler than temperature region 606b. Temperature regions 606d and 606e illustrate a fluid leak 608 that causes air to enter the drape 602. As the air enters the drape 602, the air expands and cools, which is shown by the temperature regions 606e and 606d. The air that enters the drape 602 may contact dressing beneath the drape 602 and cause the dressing to cool. The IR image 600 indicates that an opening 610 at the interface between the drape and tissue of the patient exists, thereby enabling the clinician or patient to reseal or otherwise correct the fluid leak 608.

Figure 6B:
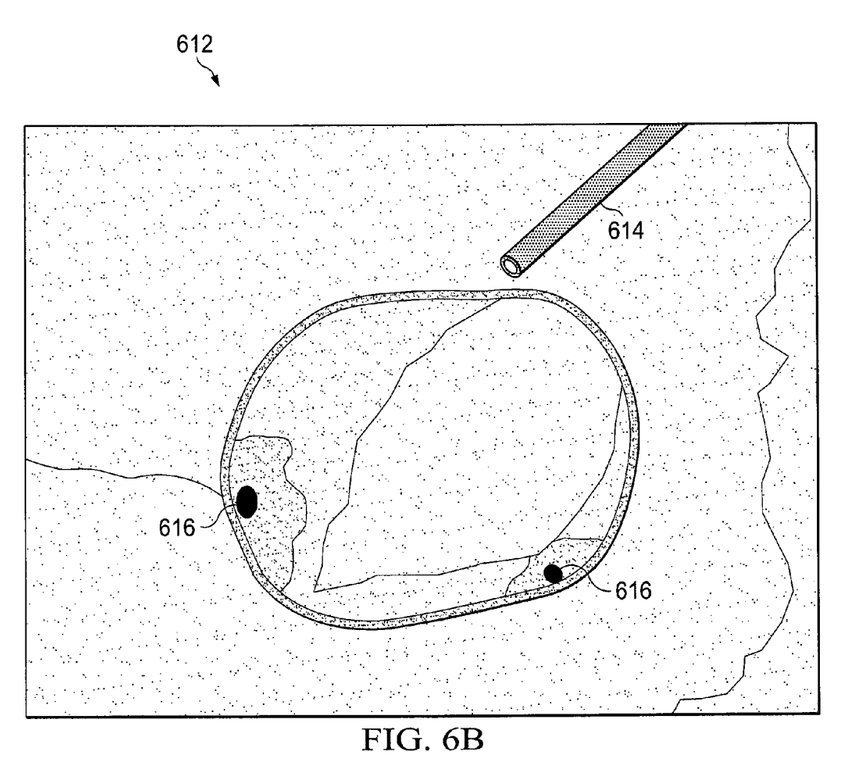
FIG. 6B is an illustration of another illustrative dressing and drape being used to treat a tissue site and in which the drape includes a fluid leak.

With regard to FIG. 6B, an illustration of an IR image 612 is shown. The IR image shows a compressed air source 614 that is used to blow compressed air around a drape that is covering a tissue site being treated by a reduced pressure delivery system. The compressed air source 614 may be compressed air or other source (e.g., an aerosol spray), as understood in the art. If a fluid leak exists between the drape and tissue, the IR camera will capture the compressed air if sucked into the drape via the interface between the drape and tissue as the compressed air expands and cools down the dressing (e.g., foam). Temperature regions 616, which appear to be two dark spots on opposite sides of the drape in the IR image, indicate precisely where fluid leaks of the drape exist, thereby enabling a clinician to correct the fluid leak. To enable the clinician to more easily identify and locate the fluid leak, the camera that includes an IR sensor or have the ability to sense IR spectral frequencies may be dynamic in that as temperatures change, the image being captured changes in a substantially real-time manner (i.e., as the temperature changes, so does the IR image).

It should be understood that the principles of the present invention provide for alternative gases other than compressed air or uncompressed air to be utilized for identifying fluid leaks in the drape. For example, carbon dioxide ($CO_2$), butane, fluorocarbons, or any other gas may be utilized to assist a clinician identify a fluid leak. As the gases are sucked into the draped area, the gases expand and cool the dressing, thereby enabling the camera with the IR sensor to detect that the dressing and/or drape is cooling. Although the camera is described as including an IR sensor, it should be understood that other sensors, such as UV or other non-visible spectral frequency sensor, may be utilized in accordance with the principles of the present invention. In one embodiment, depending on the gas used, a sensor that is sensitive to spectral radiation resulting from the gas expanding may be utilized.

As previously described, the use of pressure sensitive coatings (e.g., paints, dyes, or other coatings) may be utilized in accordance with the principles of the present invention. As understood in the art, the coatings change color as gas pressure changes. The coating detects pressure indirectly by reacting with oxygen (i.e., measures oxygen concentration), a reaction that enhances the inherent fluorescence of the pressure sensitive coating, which results in a color change. In operation, the dressing coated with a pressure or temperature sensitive coating may be exposed to either oxygen rich or oxygen depleted gas to enhance the color change of the coating and locate the fluid leak source. The coating may be applied to a dressing component (e.g., foam), drape, or adhesive. Still yet, the coating may be applied to another element that may be inserted between the drape and dressing.

Figure 7:
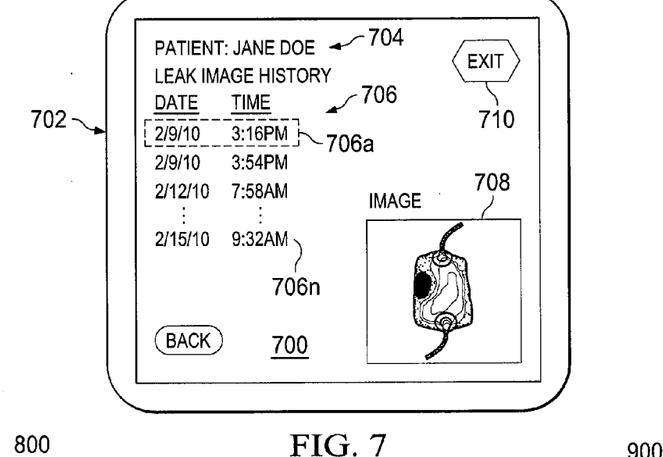
FIG. 7 is a screen shot of an illustrative graphical user interface that enables a clinician to select to view "leak image history" associated with a patient and an image associated with each leak.

With regard to FIG. 7, a screen shot of an illustrative graphical user interface 700 on a reduced pressure delivery system 702 is shown. The graphical user interface 700 may display a patient's name 704 with whom a leak image history 706 may be associated. The leak image history 706 may provide a list of selectable leak images 706a-706n that are listed in chronological order. Each of the leak images may be timestamped. In one embodiment, the timestamp may be displayed directly on the images. Alternatively and/or additionally, the timestamps may be associated with the images such that the timestamps are used to form the leak image history 706, as shown. In an alternative embodiment, rather than using timestamps for the list, image names, image thumbnails, or other indicia may be utilized to enable a clinician to select to view a leak image. Additional information may also be collected and associated with each leak image, such as clinician name, employee number, or otherwise that enables other caregivers to identify which clinician attended to correcting drape leaks. In addition, an image 708 that was collected by the clinician may be displayed in response to a clinician selecting one of the leak images 706. The leak image history may provide clinicians valuable data for both treatment and liability purposes. Once complete, the clinician may select an "exit" soft-button 710 to return to a previous graphical user interface.

Figure 8:
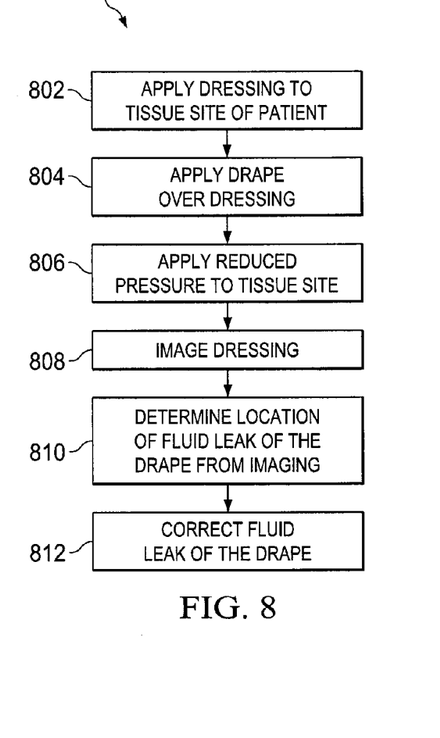
FIG. 8 is a flow chart of an illustrative process for determining location of a fluid leak of a drape at a tissue site of a patient.

With regard to FIG. 8, a flow diagram of an illustrative process 800 that enables a clinician to locate a leak of a drape being used by a reduce pressure delivery system is shown. The process 800 starts at step 802, where a dressing is applied to a tissue site of a patient. The dressing may include a manifold, foam, or any other elements used for treating a tissue site, as understood in the art. At step 804, a drape is applied over the dressing. The drape may be transparent to enable a clinician to view the dressing and/or tissue site to watch for infection or other issues with the tissue site. The drape may further include an adhesive at or near the perimeter of the drape to maintain contact with tissue surrounding the tissue site, thereby providing a sealed environment for the reduced pressure delivery system to provide for reduced pressure at the tissue site. At step 806, reduced pressure may be applied to the tissue site so as to promote tissue growth, as understood in the art.

At step 808, the dressing may be imaged. In imaging the dressing, a digital imaging system, such as a digital camera, may be utilized. The digital camera may be configured to take still or video images. In accordance with the principles of the present invention, the imaging may be performed in a non-visual spectrum. For example, the imaging may be in an IR or UV spectrum. At step 810, a clinician may visually determine location of a fluid leak of the drape from the imaging. If, for example, IR imaging is being used, as fluid, such as compressed air, is being sucked into the tissue site between an interface of the drape and tissue due to the reduced pressure, the fluid may cool down the dressing, drape, and/or tissue site such that the clinician can visually locate where fluid leak(s) are located. Using UV imaging enables the clinician to apply a fluid, such as fluorocarbons or other gas that generates a UV spectral signal, to the perimeter of the drape, and, if a fluid leak of the drape exists, when the fluid enters the drape, the UV imaging is captured and displayed. At step 812, the clinician may correct the fluid leak of the drape. In one embodiment, the clinician may be prompted or otherwise alerted to perform a leak location as a result of the reduced pressure delivery system determining that a fluid leak exists. In response, the clinician may interface with the reduced pressure delivery system to cause the system to enter a leak location mode or otherwise notify the system that the clinician is responding to the leak location notice. Such steps may occur between steps 806 and 808. The reduced pressure delivery system may also provide a user interface feature that enables the clinician to selectively enter the leak location mode to enable the clinician to utilize the reduced pressure delivery system in locating a fluid leak of the drape.

Figure 9:
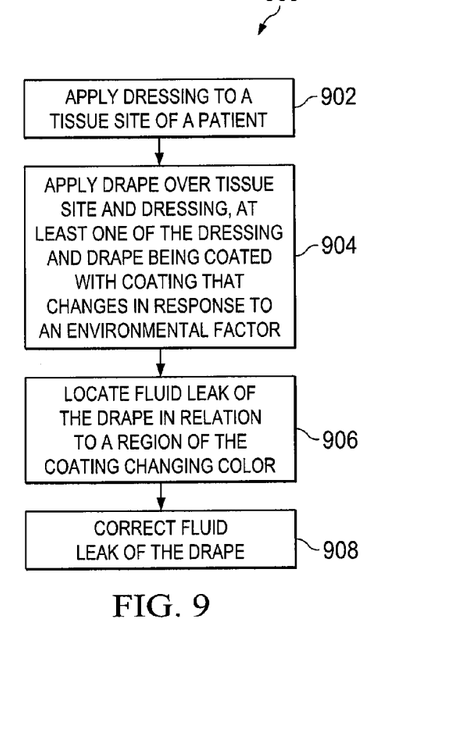
FIG. 9 is a flow chart of an alternative process for determining location of a fluid leak of a drape at a tissue site of a patient.

With regard to FIG. 9, a flow chart of an illustrative process for determining location of a fluid leak at an interface between a drape of a reduced pressure delivery system and tissue of a patient is shown. The process 900 starts at step 902, where dressing is applied to a tissue site of a patient. At step 904, a drape may be applied over the tissue site and dressing of the patient, where at least one of the dressing and drape is coated with a coating that changes color in response to an environmental factor. The environmental factor may include pressure or temperature. In other words, if either pressure or temperature changes, color of the coating changes. The coating may be a pressure or temperature sensitive coating, such as paint or dye. At step 906, a fluid leak of the drape may be located in relation to a region of the coating changing color. At step 908, correction of the fluid leak of the drape may be made. In one embodiment, to actively determine where a fluid leak of the drape exists, a fluid (e.g., compressed air, $CO_2$, fluorocarbon, or other gas) may be directed toward the interface between the drape and tissue of the patient depending on the type of sensor (e.g., IR, UV) being utilized to image the dressing. Other gases, such as butane or other gas that is identifiable by either IR or UV sensors may be utilized in accordance with the principles of the present invention. In one embodiment, the fluid may be stored and directed toward the interface in an aerosol form. In the same or similar manner as described with respect to FIG. 8, the clinician may notified by the reduced pressure delivery system that a fluid leak exists and be assisted by the reduced pressure delivery system to locate a fluid leak of the drape. Such steps may occur between steps 904 and 906.

Although the imaging sensor is described as being located outside the drape, it should be understood that the principles of the present invention may provide for one or more imaging sensors to be positioned within a drape. Such an embodiment may have imaging sensor(s) directed toward an interface of the drape and tissue from within the dressing or sandwiched between the drape and dressing. Image data collected by the imaging sensor(s) may be wired or wirelessly communicated to a remote device, such as a reduced pressure delivery system or mobile device, such as a mobile telephone executing an application configured to display the image data. Alternatively, an array of temperature sensors may be disposed within the drape for collecting temperatures or temperature differentials.

It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of this invention. The scope of the present invention is instead defined by the following claims.

We claim:

1. A system for determining location of a fluid leak at a drape of a reduced pressure delivery system being used on a tissue site of a patient, said system comprising:
   a processing unit configured to control operation of the reduced pressure delivery system and process image data;
   an input/output (I/O) unit in communication with said processing unit;
   an imaging system including an image sensor for sensing frequencies in a nonvisible spectrum and configured to capture image data based on temperature variations of the drape corresponding to frequency variations in the frequencies sensed by the image sensor, wherein the imaging system is configured to communicate the image data to the I/O unit for processing unit; and
   wherein said processing unit is further configured to process the image data by identifying temperature regions based on the temperature variations in the image data and to display the temperature regions by different colors or shadings wherein one or more of the temperature regions are associated with a fluid leak.

2. The system according to claim 1, wherein the image sensor is an IR image sensor.

3. The system according to claim 1, wherein the image sensor is a UV image sensor.

4. The system according to claim 1, further comprising an aerosol spray can for use in applying fluid to the drape.

5. The system of claim 4, wherein the aerosol spray can is configured to direct an aerosol fluid toward an interface between the drape and the tissue of the patient.

6. The system of claim 5, wherein the fluid includes at least one of compressed air, $CO_2$, fluorocarbons, and butane.

7. The system of claim 1, further comprising a memory for storing the image data in association with a patient record that includes treatment history.

8. The system of claim 1, further comprising:
   a dressing applied to the tissue site; and
   wherein the drape is applied over the dressing and tissue site.

9. The system of claim 8, further comprising a coating applied to the drape that changes color in response to an environmental factor.

10. The system of claim 9, wherein the coating is a pressure-sensitive coating that changes color in response to pressure changes.

11. The system of claim 9, wherein the coating is a temperature-sensitive coating that changes color in response to temperature changes.

12. The system of claim 1, wherein the imaging system is further configured to identify one or more leak indication regions of the drape.

13. The system of claim 12, wherein the imaging system is further configured to display the one or more leak indication regions as one or more superimposed markings on the image data of the drape.

* * * * *